United States Patent
Senpuku et al.

(10) Patent No.: US 7,094,759 B2
(45) Date of Patent: Aug. 22, 2006

(54) ORAL MODIFIED SSP-5 ANTIBACTERIAL COMPOSITION

(75) Inventors: Hidenobu Senpuku, Yokohama (JP); Yumiko Masuzawa, Tokyo (JP); Junichi Okada, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 11/013,430

(22) Filed: Dec. 17, 2004

(65) Prior Publication Data

US 2005/0180928 A1  Aug. 18, 2005

(30) Foreign Application Priority Data

Dec. 19, 2003 (JP) .............................. 2003-422472

(51) Int. Cl.
| | |
|---|---|
| A61K 38/10 | (2006.01) |
| C07K 7/08 | (2006.01) |
| C07K 2/00 | (2006.01) |
| C07K 1/00 | (2006.01) |

(52) U.S. Cl. ............................ 514/14; 514/2; 530/300; 530/327; 530/333

(58) Field of Classification Search .................... None
See application file for complete search history.

(56) References Cited

U.S. PATENT DOCUMENTS 4,816,563 A * 3/1989 Wilson et al. ............... 530/344
5,019,382 A * 5/1991 Cummins, Jr. .............. 424/85.4

FOREIGN PATENT DOCUMENTS

| JP | 6-262165 | 9/1994 |
|---|---|---|
| JP | 2002-114709 | 4/2002 |
| JP | 2002-284604 | 10/2002 |
| JP | 2002-302404 | 10/2002 |

OTHER PUBLICATIONS

D.R. Demuth, et al. Infect. Immun. (1989) 57(5), pp. 1470-1475.*
P. Richterich. Genome Research (1998) 8, pp. 251-259.*
P.L. Wesche, et al. DNA Sequence (2004) 15(5/6), pp. 362-364.*
C. Lottaz, et al. Bioinformatics (2003) 19(Suppl. 2), pp. ii103-ii112.*
D. Voet and J.G. Voet. Biochemistry, 2nd Edition. (1995), p. 966.*
R.J. Lamont et al. Infect. Immun. (1991) 59(10), pp. 3446-3450.*
Donald R. Demuth, et al., "Streptococcal-Host Interactions", The Journal of Biological Chemistry, vol. 265, no. 13, XP-002330165, May 5, 1990, pp. 7120/7126.
H. Senpuku, et al., "Identification of *Streptococcus* mutans PAc peptide motif binding with human MHC class II molecules (DRB1 0802, 1101, 1401 and 1405)", Immunology, vol. 95, No. 3, XP-008028150, 1998, pp. 322-330.
Donald R. Demuth, et al., "Comparison of *Streptococcus* Smutans and *Streptococcus sanguis* receptors for human salivary agglutinin", Microbial Pathogenesis, vol. 9, No. 3, XP-002330166, 1990, pp. 199-211.

* cited by examiner

*Primary Examiner*—Bruce R. Campell
*Assistant Examiner*—Andrew D. Kosar
(74) *Attorney, Agent, or Firm*—Oblon, Spivak, McClelland, Maier & Neustadt, P.C.

(57) ABSTRACT

The present invention provides a composition for an oral cavity that contains the amino acid sequence of SEQ ID NO: 1, which is safe and effective without imparting bacterial resistance.

22 Claims, No Drawings

SEQUENCE LISTING

```
<160> NUMBER OF SEQ ID NOS: 1

<210> SEQ ID NO 1
<211> LENGTH: 13
<212> TYPE: PRT
<213> ORGANISM: Streptococcus sanguis

<400> SEQUENCE: 1

Asp Tyr Gly Ala Lys Leu Ala Ala Tyr Gln Lys Glu Leu
1               5                   10
```

ORAL MODIFIED SSP-5 ANTIBACTERIAL COMPOSITION

BACKGROUND OF THE INVENTION

1. Field of the Invention

The present invention relates to a composition for an oral cavity, which suppresses initial adhesion of intraoral bacteria to teeth and periodontal tissue. The present invention further proves a method of preventing formation of a biofilm in an oral cavity.

2. Description of the Conventional Art

A biofilm is a film covering the surface of a microbial cell in conjunction with a substance or a precipitate secreted by bacteria when microorganisms (i.e., bacteria or the like) adhere to the surface of an object or an organism tissue and proliferate. An example of a typical biofilm in an oral cavity is plaque (bacterial plaque).

The genesis of oral cavity biofilm formation of the biofilm is an organic ingredient, such as protein or the like, in saliva coming into contact with the enamel surface, followed by a part of the organic ingredient adhering to the enamel, and thereby forming a pellicle. When an intraoral bacteria (e.g., Streptococcus sanguis) in the saliva comes into proximity with a tooth and contacts the pellicle, the intraoral bacteria is adsorbed to the pellicle, and a part of the bacteria adheres on the pellicle as it is. The adhered intraoral bacteria grows to the strong biofilm adhering to other bacteria. The adhesion of the other bacteria typically results from polysaccharides having tacky adhesiveness. These polysaccharides are knows as glucan or fructan and are made by using the nutrient or the like in the saliva. Subsequently, the bacteria in the biofilm repeats the proliferation to produce acid. Thereby, dental caries, periodontal disease or the like results.

Various method shave been researched to solve these problems. For example, an antibacterial agent and its assistant agent were proposed. As the assistant agent, antibacterial and antifungal assistants were proposed as a composition for an oral cavity including a biofilm suppressing assistant such as xylitol, farnesol or the like (for example, refer to Japanese Patent Laid Open No. 2002-302404, 2002-284604). However, since these antibacterial and antifungal assistants primarily serve to remove the biofilm, use of the antibacterial agent is indispensable.

It is known that the antibacterial agent problematically generates bacterial resistance and also sterilizes indigenous bacteria existing in the oral cavity. Therefore, there are limits to the use of antibacterial agents in a composition for an oral cavity.

Additional studies have attempted to add a protease, which is an enzyme decomposing protein, to an oral composition (for example, refer to Japanese Patent Laid Open No. 06-262165). However, since a protease is an enzyme, and as such there are problems associated with the time required to produce an effective result. Further, since proteases do not generally discriminate on the basis of protein identity beneficial proteins contained in the saliva are also decomposed.

Another attempt at solving the aforementioned problems have centered on the use of monoclonal antibodies (for example, refer to Japanese Patent Laid Open No. 2002-114709). The monoclonal antibody suppresses glucosyltransferase, which is enzyme secreted by Streptococcus mutans bacteria when producing glucan. However, if the biofilm is already formed, the effect with respect to the proliferation of the intraoral bacterial is hardly obtained. Additionally, the use of monoclonal antibodies also raises safety concerns since the monoclonal antibody originating in the mouse is applied to the inside of an oral cavity of person.

SUMMARY OF THE INVENTION

The primary objective of the present invention is to provide a composition for an oral cavity that does not impart resistance to the objective bacteria, is safe for a human body, and is effective within a short time. Further, it is also an objective that this composition effectively suppress the formation of the biofilm, but does not react with indigenous bacteria and saliva that are not related to the formation of the biofilm in an oral cavity.

The earnest work was carried out and, as the result, a peptide comprising a specific amino acid sequence that is capable of suppressing the formation of the biofilm was found, by taking notice of the following point. That is, when the intraoral bacteria forming the biofilm is not sterilized but a substance suppressing an initial adhesion of bacteria to the oral cavity tissue is used, the formation of the biofilm can be suppressed. Then, the investigation was completed.

More particularly, it is known that Streptococcus bacteria in the intraoral bacteria has a strong initial adhesion to the oral cavity tissue, for example a tooth surface covered with the pellicle. The biofilm is formed by adhesion of these bacteria to the pellicle on the tooth surface giving opportunities for further adhesion of other bacteria. Therefore, it is important to suppress the initial adhesion of the Streptococcus bacteria to the oral cavity tissue. For example, it was confirmed that the initial adhesion of the Streptococcus mutans depends on protein existing on the surface of bacteria, which is called as PAc (Protein Antigen Serotype C) with the molecular weight of about 190,000.

The present inventors researched the initial adhesion based on the A area of the PAc. On the basis of this research, it was determined that a specific peptide part (hereinafter, referred to as SSP-5(390–402)) in the protein is directly related to the initial adhesion of the Streptococcus intraoral bacteria to the tooth surface. This SSP-5(390–402) represents one fragment of the protein on the surface of the Streptococcus sanguis bacteria and has the sequence shown in SEQ ID NO: 1, wherein the residue corresponding to position 400 in SSP-5 (residue 11 in SEQ ID NO: 1) is a threonine. The present inventors have modified the original SSP-5 by isolated from Streptococcus sanguis bacteria for the further discussion herein (hereinafter, referred to as SEQ ID NO: 1 or modified SSP-5(390–402)).

As a result, when this peptide comprising the specific amino acid sequence is previously applied to the inside of an oral cavity, such as the tooth surface or the like, this peptide can block the tooth surface from Streptococcus intraoral bacteria adhering thereon, because the Streptococcus intraoral bacteria usually adhere on the tooth surface using this peptide fragment but cannot adhere since the tooth surface has already been covered by this peptide fragment. Thus it is possible to effectively suppress the initial adhesion of bacteria in a short time.

Therefore, one object of the present invention is to provide a composition for an oral cavity, which contains a peptide comprising SEQ ID NO: 1.

The composition for an oral cavity according to the present invention provides a safety advantage when administered to a host organism as compared with the conventional antibacterial agent since the composition of the present invention is based on amino acids. When the composition according to the present invention is applied to the tooth surface or the like, the composition can effectively suppress the initial adhesion of bacteria in a short time, because the peptide covers the tooth surface for blocking before the bacteria are placed in contact with the tooth surface. Further, the composition according to the present invention is an excellent composition for an oral cavity capable of effectively suppressing the formation of the biofilm without reacting to indigenous bacteria and saliva at all. These indigenous bacteria and saliva do not relate to the formation of the biofilm in an oral cavity.

DETAILED DESCRIPTION OF PREFERRED EMBODIMENT

The method of producing the peptide comprising the specific amino acid sequence (modified SSP-5(390–402)) used in the composition for an oral cavity according to the present invention it is not limited. However, an amino acid synthesizer is preferably used. At the time of synthesizing the peptide, it is important that the peptide does not contain an excessive amino acid sequence beyond that of SEQ ID NO: 1. If there is a part of the excessive amino acid sequence, the original effect for suppressing the formation of the biofilm cannot be obtained. Of course, a nonspecific peptide with respect to the initial adhesion of bacteria, which does not prevent the effect of the present invention, may be connected to one end or both ends of SEQ ID NO: 1.

The composition for an oral cavity according to the present invention can be used in various forms based on existing methodologies. The composition may be used by only blending a peptide of SEQ ID NO: 1 with water or a solvent that is safe for a human body. This composition for an oral cavity may also be used as a tooth powder, a toothpaste, a liquid dentifrice or the like. The other blending ingredients are not limited, so long as the blending ingredients do not prevent the function of the peptide. The ingredients conventionally used in the composition for an oral cavity can be blended freely. More particularly, when preparing a toothpaste, abrasives, caking additives, wetting agents, sweeteners, perfumes, antiseptics, other pharmaceutically effective agents or the like can be suitably used.

More particularly, when preparing a tooth powder, the peptide of SEQ ID NO: 1 may be blended to the abrasives, such as calcium carbonate, calcium silicate, a silica fine powder, amorphous water-containing silica, hydrophobic silica, calcium secondary phosphate, calcium pyrophosphate, insoluble sodium metaphosphate, aluminum hydroxide, silicic acid anhydride, or the like.

When preparing a toothpaste, the peptide of SEQ ID NO: 1 may be blended using the following as a base material in general. Base materials for this purpose include water, glycerin, ethylene glycol, diethylene glycol, polyethylene glycol, propylene glycol, polypropylene glycol, sorbitol, xylite, lactite, mannitol, ethanol, sodium lactate or the like. To the base material, the abrasives used to the tooth powder may be blended, if necessary.

Further, various kinds of a surfactant, such as an anionic surfactant, a nonionic surfactant, an amphoteric surfactant, a semipolar surfactant or the like, and a thickener may be suitably blended.

Examples of the anionic surfactant are an α-sulfofatty acid alkyl ester or its water-soluble salt, an alkyl sulfate ester salt, an N-acylamino acid salt, or the like.

Examples of the nonionic surfactant are a fatty acid monoglyceride, a fatty acid alkanol amide, a polyoxyethylene sorbitan fatty acid ester, a polyoxyethylene hardened castor oil, a saccharide fatty acid ester, or the like.

As the amphoteric surfactant, an alkylbetanine, imidazolinium betaine, a sulfobetaine, or the like are used.

As the semipolar surfactant, an alkylamine oxide or the like is used.

Examples of the thickener are sodium alginate, propylene glycol alginate ester, carboxymethyl cellulose, carboxymethylcellulose sodium, carboxy methylcellulose calcium, starch sodium glycolate, starch phosphate ester sodium, sodium polyacrylate, carboxypolymethylene, methylcellulose, crystalline cellulose, hydroxypropylcellulose, polyvinyl pyrrolidone, guar gum, carob bean gum, Tara gum, tamarind seed gum, gum Arabic, tragacanth gum, karaya gum, alginic acid, carrageenan, xanthan gum, gellan gum, curdlan, lactose, chitin, chitosan, chitosamine, or the like.

Further, a germicide, an antiinflammatory agent, a phosphoric acid compound and inorganic salts may be blended as pharmaceutically effective ingredients.

Examples of the germicide are sodium monofluorophosphate, sodium fluoride, chlorhexidine salts, benzethonium chloride, cetylpyridinium chloride, benzalkonium chloride, or the like.

As the antiinflammatory agent, allantoinate or the like is used.

Examples of the phosphoric acid compound are sodium phosphate, sodium pyrophosphate, sodium tripolyphosphate, sodium tetrapolyphosphate, or the like.

As the inorganic salts, sodium chloride or the like is used.

Of course, a coloring matter, a presevative or the like may be added to the composition for an oral cavity according to the present invention.

The composition for an oral cavity according to the present invention can be used as dental cleaning agents or medicines other than the above-mentioned kinds of tooth powder and toothpaste. These dental cleaning agents or medicines include a mouthwash, a chewing gum, a gargle, a troche, a cream, an ointment, a pasting agent and a tablet.

As for the peptide comprising the specific amino sequence (SEQ ID NO: 1) in the composition for an oral cavity according to the present invention, the blending amount is 0.001–20% by weight preferably, and more preferably 0.01–5% by weight.

Where the composition is a medicine, the amount of the peptide when used for internal use ranges from 5–50 mg per adult per day, and the amount of the peptide when used for external use is 1 to several 10 mg a time.

The peptide of the present invention can be used for preventing the dental caries or periodontal disease without giving harmful side effects. In the case of the tooth powder, the toothpaste or the like, the peptide can be used according to the ordinary method, considering these usage amounts.

EXAMPLE

Hereinafter, the composition for an oral cavity according to the present invention is explained with examples more concretely. However, the present invention is not limited to the following examples.

Example 1

<<Synthesis of the Peptide>>

A peptide comprising an amino acid sequence of SEQ ID NO: 1 was obtained by a stepwise solid-phase peptide synthetic method. The synthesis was conducted with a reversed phase HPLC (0.1% TFA of gradient of 10–45% acetonitrile) with a TSK-GEL column (30×1), by using Model 350 Multiple Peptide Synthesizer (Advanced Chemitech, Louisville, Ky., USA) as a synthesizer. The final purification degree was determined to be 95% or more, by using reversed phase HPLC.

<<Confirmation of Adhesion Suppressing Properties>>

<Preparation of Bacteria>

S. sanguis (ATCC10556, ATCC10558), S. mutans (ATCC25175) were used as intraoral bacteria. All bacteria were cultured under an anaerobic conditions using Brain Heart Infusion broth (BHI; Difco Lavoratory, Detroit, Mich.) as a culture medium.

<Preparation of Saliva>

The specimen was stimulus saliva secreted by biting paraffine wax for 3 minutes by 3 subjects (A, B, C). The saliva was collected, incubated at 4° C. for 5 minutes, and centrifuged at 10000×g for 10 minutes at 4° C. Then, the supernatant was used the saliva specimen.

<Sensor Chip>

The adhesion suppressing properties of bacteria was confirmed by using a sensor chip as a substitute for a tooth. As the sensor chip, Pioneer Sensor Chip F1 (produced by BIAcore Company) was used. The sensor chip F1 was activated at flow speed of 10 µL for 1 minute with 70 µL of 400 mM N-ethyl-N'-(3-diaethylaminoprophyl) carbodiimide and 100 mM N-hydroxy siccinimide solution. Then, the above saliva specimen was diluted 20 times, and bonded on the chip by passing 70 µL of sample over the activated chip. (Hereinafter, this chip was said to as a saliva treatment sensor chip)

<Confirmation Method of the Adhesion Suppressing Properties>

The confirmation method of the adhesion suppressing properties by BIA core™ Biosensor system (produced by BIAcore Company) will be explained. First, each bacteria is passed over the saliva treatment sensor chip at O.D.=1 (550 nm) and a flow speed of 20 µL/min. Then, the bonding state (Response Unit:RU) between the bacteria and saliva on the surface of the sensor chip was measured. The sensor chip was not carried out the peptide treatment.

Then, to the other saliva treatment sensor chip, which was different from the saliva treatment sensor chip adhered with bacteria, a modified SSP-5(390–402) peptide solution (1 mg/mL) dissolved with a phosphate buffer solution (PBS, pH7.4) was passed over the sensor chip at flow speed of 10 µL/min, and the surface of the saliva treatment sensor chip was treated with the peptide. Then, each bacteria was passed over the chip at O.D.=1 (550 nm) and flow speed of 20 µL/min, and the bonding state (Response Unit:RU) between each bacteria and saliva on the sensor surface was measured. The final bacterium adhesion suppressing ratio by the peptide treatment was measured using the following formula 1.

Adhesion suppressing ratio=100×{[Bonding state between bacteria and saliva (RU)]−[Bonding state between bacteria and saliva (after the peptide treatment) (RU)]}/[Bonding state between bacteria and saliva (RU)]   [Formula 1]

TABLE 1

| Saliva sample | Adhesion suppressing ratio | | |
|---|---|---|---|
| | S. sanguis (ATCC10556) | S. sanguis (ATCC10558) | S. mutans (ATCC25175) |
| A | 61% | 59% | 55% |
| B | 57% | 63% | 60% |
| C | 65% | 61% | 58% |

Example 2

As the composition for an oral cavity containing the peptide of SEQ ID NO: 1, the toothpaste was prepared with following compositions. The adhesion suppressing properties of bacterial plaque was evaluated by the experiment described below.

| | |
|---|---|
| Calcium carbonate | 40% by weight |
| Sodium carboxymethyl cellulose | 1.0% by weight |
| Glycerin | 8.0% by weight |
| Sodium lauryl sulfate | 1.5% by weight |
| Sorbitol | 10.0% by weight |
| Menthol | 0.3% by weight |
| Peptide comprising a specific amino sequence | 1.0% by weight |
| Water | 38.2% by weight |

Example 3

As the composition for an oral cavity containing the peptide of SEQ ID NO: 1, a tablet-shaped composition for an oral cavity was prepared with following compositions. The adhesion suppressing properties of bacterial plaque was evaluated by the experiment described below.

| | |
|---|---|
| Lactose | 65% by weight |
| Crystalline cellulose | 26% by weight |
| Magnesium stearate (lubricant) | 4% by weight |
| Xylitol | 3% by weight |
| Peptide comprising a specific amino sequence | 2% by weight |

The effect of the composition for an oral cavity of Example 3 was confirmed by the following method.

The method comprising, washing and polishing of the teeth surfaces of 3 subjects (A, B, C) in the dental clinic, brushing of only the left side teeth in an oral cavity of each 3 subjects after 3 time meals per day by using the toothpaste of Example 2, brushing of the right side teeth using a toothpaste, in which water was blended instead of the peptide comprising the specific amino sequence of Example 2, measuring of bacterial plaques of left and right side teeth with eyes by using a dyeing method with a dye for an oral cavity (PROSPEC GEL, produced by GC Corporation) after one weak, and comparing of these bacterial plaques. These results were shown in Table 2 collectively.

TABLE 2

| Subjects | Left side in an oral cavity | Right side in an oral cavity |
| --- | --- | --- |
| A | Bacterial plaque is hardly dyed | Bacterial plaque is colored red a little and can be confirmed |
| B | Bacterial plaque is hardly dyed | Bacterial plaque is colored red a little and can be confirmed |
| C | Bacterial plaque is hardly dyed | Bacterial plaque is colored red a little and can be confirmed |

The effect of the composition for an oral cavity of Example 3 was confirmed by the following method.

The method comprising, washing and polishing of the teeth surfaces of 3 subjects (D, E, F) in the dental clinic, brushing of the teeth of each 3 subjects 3 times per day without using the toothpaste, and confirming of the amounts of bacterial plaques by the dyeing method after one weak like the above-mentioned method. Then, the evaluation was continued by the method comprising, washing and polishing of the teeth surfaces of 3 subjects in the dental clinic again, brushing of the teeth after 3 time meals per day without using the toothpaste, eating the tablet-shaped composition for an oral cavity of Example 3 3 times per day, and confirming of the amounts of bacterial plaques by the dyeing method with the dye for an oral cavity (PROSPEC GEL, produced by GC Corpotation) after one weak. These results were shown in Table 3 collectively.

TABLE 3

| Subjects | Composition for an oral cavity was not used | Composition for an oral cavity was used |
| --- | --- | --- |
| D | Bacterial plaque is colored red a little and can be confirmed | Bacterial plaque is hardly dyed |
| E | Bacterial plaque is colored red a little and can be confirmed | Bacterial plaque is hardly dyed |
| F | Bacterial plaque is colored red a little and can be confirmed | Bacterial plaque is hardly dyed |

2. The composition according to claim 1, wherein the concentration of said peptide is 0.001–20% by weight based upon the total weight of the composition.

3. The composition according to claim 1, wherein said composition is in a form suitable for oral administration.

4. The composition according to claim 3, wherein said form suitable for oral administration is selected from the group consisting of a tooth powder, a toothpaste, a liquid dentifrice, mouthwash, a chewing gum, a gargle, a troche, a cream, an ointment, a pasting agent and a tablet.

5. The composition according to claim 4, wherein said form suitable for oral administration is a toothpaste and said toothpaste further comprises one or more additives selected from the group consisting of abrasives, caking additives, wetting agents, sweeteners, perfumes, antiseptics, and other pharmaceutically effective agents.

6. The composition according to claim 4, wherein said form suitable for oral administration is a toothpaste and said toothpaste further comprises one or more base materials selected from the group consisting of water, glycerin, ethylene glycol, diethylene glycol, polyethylene glycol, propylene glycol, polypropylene glycol, sorbitol, xylite, lactite, mannitol, ethanol, and sodium lactate.

7. The composition according to claim 1, further comprising one or more abrasives selected from the group consisting of calcium carbonate, calcium silicate, a silica fine powder, amorphous water-containing silica, hydrophobic silica, calcium secondary phosphate, calcium pyrophosphate, insoluble sodium metaphosphate, aluminum hydroxide, and silicic acid anhydride.

8. The composition according to claim 1, further comprising one or more surfactants selected from the group consisting of an anionic surfactant, a nonionic surfactant, an amphoteric surfactant, and a semipolar surfactant.

9. The composition according to claim 8, wherein said one or more surfactants is at least one anionic surfactant and said anionic surfactant is selected from the group consisting of an α-sulfofatty acid alkyl ester, a water-soluble salt of an α-sulfofatty acid alkyl ester, an alkyl sulfate ester salt, and an N-acylamino acid salt.

10. The composition according to claim 8, wherein said one or more surfactants is at least one nonionic surfactant and said nonionic surfactant is selected from the group consisting of a fatty acid monoglyceride, a fatty acid alkanol

What is claimed is:

1. A composition comprising a peptide consisting of the amino acid sequence of SEQ ID NO: 1.

amide, a polyoxyethylene sorbitan fatty acid ester, a polyoxyethylene hardened castor oil, and a saccharide fatty acid ester.

11. The composition according to claim 8, wherein said one or more surfactants is at least one amphoteric surfactant and said amphoteric surfactant is selected from the group consisting of an alkylbetanine, imidazolinium betaine, and a sulfobetaine.

12. The composition according to claim 8, wherein said one or more surfactants is at least one semipolar surfactant and said semipolar surfactant is an alkylamine oxide.

13. The composition according to claim 1, further comprising one or more thickeners selected from the group consisting of sodium alginate, propylene glycol alginate ester, carboxymethyl cellulose, carboxymethylcellulose sodium, carboxy methylcellulose calcium, starch sodium glycolate, starch phosphate ester sodium, sodium polyacrylate, carboxypolymethylene, methylcellulose, crystalline cellulose, hydroxypropylcellulose, polyvinyl pyrrolidone, guar gum, carob bean gum, Tara gum, tamarind seed gum, gum Arabic, tragacanth gum, karaya gum, alginic acid, carrageenan, xanthan gum, gellan gum, curdlan, lactose, chitin, chitosan, and chitosamine.

14. The composition according to claim 1, further comprising at least one pharmaceutically effective ingredient selected from the group consisting of a germicide, an antiinflammatory agent, a phosphoric acid compound and an inorganic salt.

15. The composition according to claim 14, wherein said at least one pharmaceutically effective ingredient is at least one germicide and said germicide is selected from the group consisting of sodium monofluorophosphate, sodium fluoride, chlorhexidine salts, benzethonium chloride, cetylpyridinium chloride, and benzalkonium chloride.

16. The composition according to claim 14, wherein said at least one pharmaceutically effective ingredient is an antiinflammatory agent and said antiinflammatory agent is allantoinate.

17. The composition according to claim 14, wherein said at least one pharmaceutically effective ingredient is at least one phosphoric acid compound and said phosphoric acid compound is selected from the group consisting of sodium phosphate, sodium pyrophosphate, sodium tripolyphosphate, and sodium tetrapolyphosphate.

18. The composition according to claim 14, wherein said at least one pharmaceutically effective ingredient is an inorganic salt and said inorganic salt is sodium chloride.

19. The composition according to claim 1, further comprising at least one coloring matter or at least one preservative, or mixtures thereof.

20. The composition according to claim 4, wherein said form suitable for oral administration is a medicine and said peptide is contained in said medicine at a quantity ranging from 5 to 50 mg.

21. A method of dental cleaning comprising contacting one or more teeth of a subject in need thereof with a composition according to claim 1.

22. A method of preventing biofilm formation comprising contacting one or more teeth of a subject in need thereof with a composition according to claim 1.

* * * * *